United States Patent
Selm et al.

(10) Patent No.: US 7,335,669 B2
(45) Date of Patent: Feb. 26, 2008

(54) USE OF DIHYDROQUINOLINE TO AID IN INCREASING MILK PRODUCTION AND FEED UTILIZATION

(75) Inventors: Thomas J. Selm, Manchester, MO (US); Dana H. Saylor, St. Louis, MO (US)

(73) Assignee: Novus International, Inc., St. Louis, MO (US)

( * ) Notice: Subject to any disclaimer, the term of this patent is extended or adjusted under 35 U.S.C. 154(b) by 614 days.

(21) Appl. No.: 10/376,520

(22) Filed: Feb. 27, 2003

(65) Prior Publication Data

US 2003/0162809 A1   Aug. 28, 2003

Related U.S. Application Data

(60) Provisional application No. 60/359,823, filed on Feb. 27, 2002.

(51) Int. Cl.
*A61K 31/47*   (2006.01)

(52) U.S. Cl. .............. 514/312; 424/438; 424/442; 426/807

(58) Field of Classification Search ............. 514/311, 514/312; 424/438
See application file for complete search history.

(56) References Cited

U.S. PATENT DOCUMENTS

| | | | |
|---|---|---|---|
| 4,079,153 A | 3/1978 | Coleman | |
| 4,087,561 A | 5/1978 | Bharucha et al. | |
| 4,088,793 A | 5/1978 | Bharucha et al. | |
| 4,305,932 A | 12/1981 | Menachemoff et al. | |
| 4,592,915 A | 6/1986 | Goyette et al. | |
| 4,871,551 A | 10/1989 | Spencer | |
| 4,952,590 A | 8/1990 | von Magius | |
| 4,986,996 A | 1/1991 | Barlow et al. | |
| 5,000,964 A | 3/1991 | McCauley, III | |
| 5,066,498 A | 11/1991 | McCauley, III | |
| 5,167,835 A | 12/1992 | Harder | |
| 5,282,379 A | 2/1994 | Harder et al. | |
| 5,348,755 A | 9/1994 | Roy | |
| 5,656,319 A | 8/1997 | Barclay | |
| 5,698,244 A | 12/1997 | Barclay | |
| 5,891,491 A | 4/1999 | Owens et al. | |
| 6,017,564 A | 1/2000 | Owens et al. | |
| 6,177,108 B1 | 1/2001 | Barclay | |
| 6,299,913 B1 | 10/2001 | Block et al. | |
| 2004/0076659 A1* | 4/2004 | Shelford et al. ............ | 424/442 |

FOREIGN PATENT DOCUMENTS

| | | |
|---|---|---|
| CA | 943962 | 3/1974 |
| CA | 944135 | 3/1974 |
| CA | 2087792 | 1/1993 |
| EP | 0 466 674 A1 | 1/1992 |
| FR | 2513491 | 9/1981 |
| GB | 955316 | 4/1964 |
| GB | 1356002 | 6/1974 |
| GB | 1440183 | 6/1976 |
| GB | 1444024 | 7/1976 |
| GB | 1537334 | 12/1978 |
| HU | 2921 | 11/1977 |
| JP | 46036625 | 2/1969 |
| JP | 48012744 | 5/1970 |
| JP | 51024421 | 7/1976 |
| JP | 58031944 | 2/1983 |
| SU | 631517 | 11/1978 |
| SU | 649396 | 2/1979 |
| SU | 679578 | 8/1979 |
| SU | 705334 | 12/1979 |
| SU | 751381 | 7/1980 |
| WO | WO 9503712 | 2/1995 |

OTHER PUBLICATIONS

Dunkley et al., Supplementing Rations With Tacopherol And Ethoxyquin To Increase Oxidative Stability Of Milk, J. Dairy Science, 50(4):492-499, Jul. 1997.

Dunkley et al., Compounds In Milk Accompanying Feeding Of Ethoxyquin, J. Dairy Science, 41(8):1215-1218, Jul. 1997.

* cited by examiner

*Primary Examiner*—Neil S. Levy

(57) ABSTRACT

Milk production and feed efficiency are improved by feeding the animal producing the milk a diet of feed comprising a substituted 1,2-dihydroquinoline compound.

8 Claims, No Drawings

USE OF DIHYDROQUINOLINE TO AID IN INCREASING MILK PRODUCTION AND FEED UTILIZATION

RELATED APPLICATION DATA

This application claims the benefit of application Ser. No. 60/359,823 filed Feb. 27, 2002.

BACKGROUND OF THE INVENTION (1) Field of the Invention

The present invention relates to enhancement in milk production, and more particularly to such improvement by application of dihydroquinoline compounds to the feed of lactating animals.

(2) Description of the Prior Art

The dairy industry is always searching for techniques for increasing the production of milk from dairy cows. In particular, the industry is always searching for ways to increase milk production on a per cow basis—that is, volume of milk produced per cow—as well as ways to increase milk production on a feed efficiency basis—that is, volume of milk per pound of feed.

Ethoxyquin (6-ethoxy-1,2-dihydro-2,2,4-trimethylquinoline) has been applied to the feed of cattle, but for reasons other than for increasing milk production. For example, U.S. Pat. No. 6,017,564 describes a method for improving health, feed efficiency (that is, weight gain per pound of feed consumed) or weight gain of cattle that have been stressed, such as by their shipping or deprivation of food and/or water, by adding ethoxyquin to their feed. In particular, that patent discusses the treatment of receiving cattle upon their arrival at the feed yard and focuses on beef cattle wherein the primary goal is health and weight gain of the cattle prior to slaughter. U.S. Pat. No. 5,891,491 also discloses a method that involves incorporating ethoxyquin in cattle feed. There, the ethoxyquin is used to extend the shelf life of beef derived from the cattle.

Ethoxyquin also has been reported to have been used in a concentration of 0.05 to 0.1% (500-1,000 ppm) in a feed composition for breeding cattle with N3 fatty acid-accumulated beef. See Canadian Patent No. 2,087,792. According to page 10 of that Canadian patent, the ethoxyquin is used as an anti-oxidant and "also plays an anti-oxidation activity in the cattle's body, as well as in the feed composition, to prevent the oxidative decomposition of N3 fatty acid in spoilage of feed during long-term storage." And, in U.K., Patent No. 144,024, the possible candidacy of ethoxyquin as an anti-oxidant component of a food or feed supplement to prevent the occurrence of or to retard cancer is reported. It is suggested there that the ethoxyquin concentration should be sufficient for the daily consumption to be about 0.01 to 500 mg.

Ethoxyquin has been reported to have been added at a rate of from about 125 ppm by weight to about 150 ppm by weight on a dry matter intake ("DMI") basis to the diets of dairy cattle to reduce the oxidized flavor of milk, but the dietary ethoxyquin in those trials has been reported to result in the appearance of ethoxyquin in the fat of the resulting milk, while the tolerance of ethoxyquin in milk is zero. Dunkley et al., Supplementing Rations with Tocopherol and Ethoxyquin to Increase Oxidative Stability of Milk, J. Dairy Sci., Vol. 50, No. 4, pp. 492-499 (1967) ("Dunkley I"); Dunkley et al., Compounds in Milk Accompanying Feeding of Ethoxyquin, J. Dairy Sci., Vol. 51, No. 8, pp. 1215-1218 (1968).

Dietary ethoxyquin also has been applied to animals other than cattle. For example, it has been reported to reduce or to prevent certain maladies associated with a deficiency of Vitamin E, in particular, encephalomalacia, exudative diathesis in chicks, muscular dystrophy in chicks and lambs and fetal resorption in rats. It is unclear whether these effects have been direct effects on the target tissues or indirect effects through preventing lipid oxidation and reducing Vitamin E usage or by preventing Vitamin E destruction in the diet or the gut. Miller and White, Nutr. Rep. Int. 12:245-252 (1975); Whanger et al., Nutr. Rep. Inst. 13:159-173 (1976). However, dietary ethoxyquin has been reported to prevent lipid oxidation in muscle tissues in broilers and layers. Bartov and Bornstein, Br. Poultry Sci. 18:59-68 (1977); Combs and Regenstein, Poultry Sci. 59:347-351 (1980). The ethoxyquin concentration in the feed in the broiler study was 75 to 150 ppm by weight, and 150 ppm of ethoxyquin was found to be as effective as about 15 ppm alpha-tocopherol acetate. In the layer study, the ethoxyquin concentration was 500 ppm. Ethoxyquin was detected in the muscle tissue of poultry and lambs, suggesting that the effect is directly in the tissue, demille et al., Can. J. Anim. Sci. 52:351-361 (1972).

Despite these reports of uses of ethoxyquin in feed, there has been no recognition in the industry of which applicants are aware that ethoxyquin may have any effect on the efficiency of milk production. In any event, however, the dairy industry is still searching not only for ways to improve milk production of dairy cattle, but also for ways to improve feed efficiency in milk production.

SUMMARY OF THE INVENTION

The present invention, therefore, is directed to a novel method for treating an animal such as cattle, sheep or goats, comprising feeding to the animal a diet of feed comprising, on a dry matter intake basis, from about 25 to about 100 ppm by weight of a substituted 1,2-dihydroquinoline compound of the formula

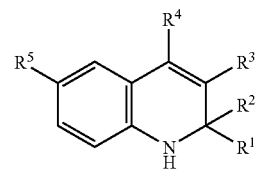

wherein $R^1$, $R^2$, $R^3$ and $R^4$ are independently selected from the group consisting of hydrogen and alkyl groups of from 1 to about 6 carbon atoms, and $R^5$ is an alkoxy group of from 1 to about 12 carbon atoms.

The present invention also is directed to a method for increasing feed efficiency of milk production, comprising feeding to a lactating mammal a diet of feed comprising, on a dry matter intake basis, from about 25 to about 100 ppm by weight of a substituted 1,2-dihydroquinoline compound of the formula

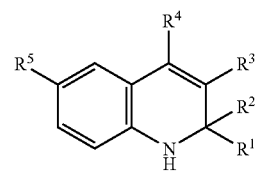

wherein $R^1$, $R^2$, $R^3$ and $R^4$ are independently selected from the group consisting of hydrogen and alkyl groups of from 1 to about 6 carbon atoms, and $R^5$ is an alkoxy group of from 1 to about 12 carbon atoms.

The present invention also is directed to a method for increasing production of milk for human consumption, comprising feeding to a lactating mammal a diet of feed comprising, on a dry matter intake basis, from about 25 to about 100 ppm by weight of a substituted 1,2-dihydroquinoline compound of the formula

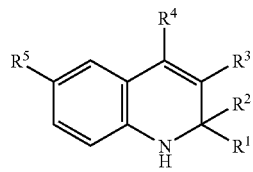

wherein $R^1$, $R^2$, $R^3$ and $R^4$ are independently selected from the group consisting of hydrogen and alkyl groups of from 1 to about 6 carbon atoms, and $R^5$ is an alkoxy group of from 1 to about 12 carbon atoms.

The present invention further is directed to a method for production of a milk product for human consumption. The method comprises feeding a lactating cow, sheep or goat a diet of feed comprising, on a dry matter intake basis, from about 25 to about 100 ppm by weight of a substituted 1,2-dihydroquinoline compound of the formula

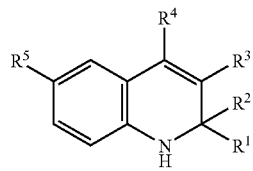

wherein $R^1$, $R^2$, $R^3$ and $R^4$ are independently selected from the group consisting of hydrogen and alkyl groups of from 1 to about 6 carbon atoms, and $R^5$ is an alkoxy group of from 1 to about 12 carbon atoms, milking the animal to produce milk and treating the milk to produce a milk product.

The present invention also is directed to such milk product itself.

Among the several advantages of this invention, may be noted the provision of a method that increases milk production in dairy cows; the provision of a method that increases feed efficiency in milk production; and the provision of such methods that increase milk production without imparting to the milk undesirable levels of a dihydroquinoline compound.

DETAILED DESCRIPTION OF THE PREFERRED EMBODIMENTS

In accordance with the present invention, it has been discovered that incorporating a substituted 1,2-dihydroquinoline compound of the formula

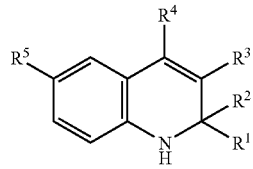

wherein $R^1$, $R^2$, $R^3$ and $R^4$ are independently selected from the group consisting of hydrogen and alkyl groups of from 1 to about 6 carbon atoms, and $R^5$ is an alkoxy group of from 1 to about 12 carbon atoms, into the feed of lactating animals, especially cattle, sheep and goats whose milk is destined for human consumption in some form, surprisingly increases the milk production of the animal, particularly as viewed on the basis of the feed efficiency of the milk production (i.e., volume of milk per pound of feed). This finding is particularly surprising because it has been discovered that the enhancement of milk production is greater at 50 ppm by weight (on an as fed basis) dihydroquinoline than it is at 125 or 150 ppm by weight (on an as fed basis) dihydroquinoline. Ordinarily, one would expect greater effect at greater concentration. Thus, in the prior art, the preferred concentrations have been considered to be the maximum permitted for use in animal feed—150 ppm. Yet, just the opposite has been found to be true within the ranges considered—50 ppm has yielded greater enhancement of milk production than has 150 ppm. Accordingly, within the range of potential dihydroquinoline concentrations, a window of relatively low concentrations has been found to be associated with optimal results. Moreover, the discovery of that window of reduced concentration not only enables increased milk production in terms of volume of milk per amount of additive, but per cow and amount of feed as well. Therefore, as used herein, references to increase or improvement in milk production refers to an increase or improvement on any of the following bases: per pound of additive, per pound of feed or per animal. Moreover, use of the dihydroquinoline at the lower levels of the present invention provides benefits not only of lower additive use (and lower cost associated with the lower additive consumption), but also of lower feed intake (and the lower cost associated therewith), greater milk production, and lower dihydroquinoline concentration in the resulting milk. This final benefit is particularly significant in view of the governmentally imposed limits on the presence of ethoxyquin in milk.

More particularly, according to the present invention, the substituted 1,2-dihydroquinoline compound is incorporated into the feed of the animal, preferably during lactation. Although the additive may be employed year-round, preferably its use is initiated within about a week of the onset of lactation and generally no more than about two (2) weeks prior to the onset of lactation and is continued throughout lactation or at least until shortly prior to the cessation of milking the animal. For dairy cattle, lactation typically lasts about three hundred days a year and so treatment for at least about three hundred days is preferred. The treatment may be repeated for each of the following years during the milking life of the cow-typically about three to four years.

According to the treatment of the present invention, the animals are fed their standard feed, except that a substituted 1,2-dihydroquinoline compound has been added to it. The substituted 1,2-dihydroquinoline compound corresponds to the formula

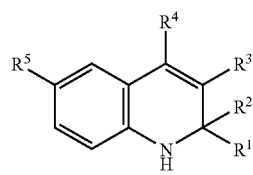

wherein $R^1$, $R^2$, $R^3$ and $R^4$ are independently selected from hydrogen and alkyl groups of from 1 to about 6 carbon atoms, preferably from 1 to four carbon atoms, and $R^5$ is an alkoxy group of from 1 to about 12 carbon atoms, preferably from 1 to four carbon atoms. The most preferred 1,2-dihydroquinoline is 6-ethoxy-1,2-dihydro-2,2,4-trimethylquinoline, commonly known as "ethoxyquin." Ethoxyquin is a well known compound, as discussed above, and is readily available. For example, one form is sold under the trademark SANTOQUIN®. The ethoxyquin may be added in wet or dry form. For the sake of brevity, the following description of the method of this invention will refer specifically to ethoxyquin, but it should be understood that it is believed that the method may be generalized to the other 1,2-dihydroquinolines defined above as well.

Because oxidation may tend to consume some ethoxyquin over time upon exposure to heat, moisture and other feed constituents, it is preferred that it be added to the feed shortly before the animal feeding, preferably within a day of feeding, more preferably within two hours of feeding, especially with high moisture diets. No further additives, such as N3 fatty acids, are required. And, whereas conventional use of ethoxyquin to prevent rancidity or spoilage of the feed itself involved addition of the ethoxyquin only to the fat or tallow ingredients of the feed, such as fish meal, in the present method, ethoxyquin is added even to the non-fat ingredients of the feed. While the ethoxyquin might be present in less than all the ingredients initially, it is desired that the ethoxyquin be dispersed through all the ingredients of the finished feed. This addition may be in combination with the mixing together of the feed ingredients to form the final diet, or after the mixing of the after ingredients. In the former case, the ethoxyquin may be simply mixed in as another feed ingredient. In the latter case, the ethoxyquin may be added to the feed mixture prior to inclusion in the final diet; for example, the ethoxyquin may be incorporated into a pre-mix, protein supplement or any other appropriate carrier.

The ethoxyquin should be incorporated into the feed to produce an ethoxyquin concentration in the feed of from about 25 to about 100 ppm, preferably about 25 to about 75 ppm, more preferably about 30 to about 50, most preferably about 35 ppm, by weight. These concentrations are based on the weight of feed in terms of dry feed (or matter) intake, as is standard in the industry for referring to concentration.

By adding the ethoxyquin to the feed shortly prior to feeding as discussed above, the apparent disappearance of ethoxyquin, most likely due to oxidation, may be able to be minimized or avoided. Thus, the desired ethoxyquin concentrations are not just initial concentrations in the feed, but in the preferred embodiment, the unoxidized ethoxyquin concentration of feed as it is ingested by the animal.

It is believed that the concentrations of ethoxyquin found to be effective with respect to cattle may be employed with other animals with similar results. Moreover, it is believed that the preferred ranges found with cattle, and particularly the optimum range, would be desirable for other animals as well. To the extent optimal dosages vary from species to species, however, optimization may be readily ascertained by those of ordinary skill in the art.

The ethoxyquin may be used as the sole feed additive, or it may be used in combination with another technique or additive. For example, if desired, the ethoxyquin might be used in combination with a nutriment, at a relative ethoxyquin to nutriment ratio of choice. Alternatively, or in addition, the resulting food product may be treated. For instance, potassium sorbate may be added to meat to inhibit bacterial spoilage.

The resulting milk from the treated animal has been found to be virtually indistinguishable from that derived from untreated animals. In particular, no ethoxyquin has been detected in milk derived from cattle treated by the method of the present invention. Of course, measurement of chemical levels has limitations. In view of that, references herein to milk being free of a dihydroquinoline means that standard detection techniques do not detect the presence of the dihydroquinoline in the milk, and references to milk being substantially free of a dihydroquinoline means that the concentration of the dihydroquinoline is less than about 0.01 ppm by weight. In any event, the level of ethoxyquin in the milk produced according to this invention certainly is less than 0.1 ppm by weight.

The milk may be processed by any standard technique, such as (but not limited to) pasteurization and homogenization, in the same manner as prior art milk. Likewise, the milk may be processed to form other milk products, such as cheese, butter, cream, and the like, by standard techniques.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples. In the example, all percentages are given on a weight basis unless otherwise indicated.

EXAMPLE 1

Each of twenty-four cows was randomly assigned to a feeding regimen of one of four concentration levels of ethoxyquin (0 ppm, 50 ppm, 100 ppm, and 150 ppm by weight on an as fed basis) for a two-week treatment period. Data were collected before and after the feeding regimen. The results were as follows, wherein the ethoxyquin concentration ("Ethox. Dose") is presented in ppm by weight, on an as fed basis and "TMR" represents the total mixed ration consumed by the cows in pounds per day:

| | Milk Production | |
|---|---|---|
| Ethox. Dose | Milk Produced During First Week (lbs./day) | Milk Produced During Second Week (lbs./day) |
| 0 | 67 | 72 |
| 50 | 79 | 82 |
| 100 | 74 | 72 |
| 150 | 70 | 74 |

| | Feed Intake (as fed basis) | |
|---|---|---|
| Ethox. Dose | TMR in First Week | TMR in Second Week |
| 0 | 94 | 93 |
| 50 | 91 | 91 |
| 100 | 92 | 91 |
| 150 | 92 | 92 |

| | Milk Production Based on Feed Efficiency (lbs. Milk Produced/pounds TMR Intake) | |
|---|---|---|
| Ethox. Dose | Lbs. Milk / TMR in First Week | Lbs. Milk / TMR in Second Week |
| 0 | 0.71 | 0.77 |
| 50 | 0.87 | 0.91 |
| 100 | 0.80 | 0.79 |
| 150 | 0.76 | 0.80 |

| | Milk Fat and Protein | | | |
|---|---|---|---|---|
| Ethox. Dose | Fat (% of Milk) in First Week | Protein (% of Milk) in First Week | Fat (% of Milk) in Second Week | Protein (% of Milk) in Second Week |
| 0 | 3 | 2.9 | 3 | 2.8 |
| 50 | 2.95 | 2.8 | 2.95 | 2.65 |
| 100 | 2.95 | 2.85 | 3 | 2.8 |
| 150 | 2.95 | 2.75 | 2.95 | 2.65 |

The variations in milk fat and protein content were considered to be well within experimental error.

EXAMPLE 2

Approximately 2400 lactating dairy cows were divided into two treatment groups of four pens per group. The cows in one of the two groups were fed ethoxyquin (at a concentration of 65 ppm by weight based on the weight of the total feed fed to the cows) for three weeks, with the four pens of the other group serving as controls. For the next two weeks, neither of the groups was fed ethoxyquin. The pens were then switched so that the previous control group was fed ethoxyquin (at a concentration of 65 ppm by weight based on the weight of the total feed fed to the cows) for three weeks. Milk production and feed intake were measured and feed efficiencies were calculated. The following table reports the means and pooled SEM results after correction for pen effects (wherein "Treated" refers to the cows receiving the ethoxyquin):

|  | Milk Production (lbs./day) | Feed Intake DMI Basis (lbs./day) | Feed Intake As Fed Basis (lbs./day) | Feed Efficiency As Fed Basis |
|---|---|---|---|---|
| Control | 83.2 | 62.6 | 97.1 | 0.85 |
| Treated | 83.4 | 60.3 | 93.5 | 0.89 |
| Pooled SEM | 0.56 | 0.5 | 0.5 | 0.05 |

The corresponding milk contents were as follows:

|  | Fat (%) | Protein (%) | Lactose (%) | SNF (%) |
|---|---|---|---|---|
| Control | 3.34 | 2.97 | 4.80 | 8.67 |
| Treated | 3.31 | 2.92 | 4.78 | 8.60 |
| Pooled SEM | 0.04 | 0.04 | 0.02 | 0.04 |

Although little difference in milk production was manifested in the trials, a reduction in feed intake resulted in a 4.7% improvement in feed efficiency in terms of pounds of milk produced per pounds of TMR intake, on a dry matter basis. The variations in milk composition were within the range of experimental error and so not significant.

In view of the above, it will be seen that the several advantages of the invention are achieved and other advantageous results obtained.

As various changes could be made in the above methods and compositions without departing from the scope of the invention, it is intended that all matter contained in the above description shall be interpreted as illustrative and not in a limiting sense.

What is claimed:

1. A method for increasing the feed efficiency of milk production, the method comprising feeding to a lactating dairy mammal selected from the group consisting of dairy cattle, dairy sheep and dairy goats, a diet of feed comprising, on a dry matter intake basis, from about 25 to about 100 ppm by weight of 6-ethoxy-1,2-dihydro-2,2,4-trimethylquinoline, wherein the pounds of milk per pound feed fed to the lactating dairy mammal is increased.

2. The method of claim 1, wherein the dairy mammal is a dairy cow.

3. The method of claim 2, wherein the feed comprises, on a dry matter intake basis, from about 50 to about 65 ppm by weight 6-ethoxy-1,2-dihydro-2,2,4-trimethylquinoline.

4. The method of claim 3, wherein the dairy cow is fed the diet for at least about 300 days a year for at least one year.

5. The method of claim 3, wherein the fed said diet for at least about 300 days a year for at least three years.

6. The method of claim 3, wherein the dairy cow produces milk comprising less than about 0.01 ppm by weight 6-ethoxy-1,2-dihydro-2,2,4-trimethylquinoline.

7. The method of claim 3, wherein the milk is substantially free of 6-ethoxy-1,2-dihydro-2,2,4-trimethylquinoline.

8. The method of claim 3, wherein the diet is initiated within about one week of the onset of a period of lactation.

* * * * *